United States Patent [19]
Wong

[11] Patent Number: 5,453,621
[45] Date of Patent: * Sep. 26, 1995

[54] ENHANCED PATHLENGTH GAS SAMPLE CHAMBER

[75] Inventor: Jacob Y. Wong, Santa Barbara, Calif.

[73] Assignee: Gaztech International Corporation, Goleta, Calif.

[*] Notice: The portion of the term of this patent subsequent to Nov. 17, 2009 has been disclaimed.

[21] Appl. No.: 301,884

[22] Filed: Sep. 7, 1994

Related U.S. Application Data

[63] Continuation of Ser. No. 49,033, Apr. 16, 1993, Pat. No. 5,414,264.
[51] Int. Cl.$^6$ ........................................... G01N 21/61
[52] U.S. Cl. .................. 250/343; 250/338.5; 356/437
[58] Field of Search ...................... 250/343, 338.5; 356/437

[56] References Cited

U.S. PATENT DOCUMENTS 4,190,363  2/1980  Adrian ..................................... 250/343
5,163,332  11/1992  Wong ..................................... 250/338.5

FOREIGN PATENT DOCUMENTS 2626642  12/1977  Germany ............................... 250/343

Primary Examiner—Carolyn E. Fields
Attorney, Agent, or Firm—Daniel C. McKown

[57] ABSTRACT

The sensitivity of a nondispersive infrared gas analyzer increases with increasing pathlength, which increases the absorption of the infrared radiation by the gas whose concentration is to be determined. The present invention includes the addition of an obstructing element that further increases the average pathlength. In one embodiment the obstructing element consists of a highly reflective elongated cylinder located with its axis collinear with the axis of the tubular chamber. In another embodiment, the sample chamber includes a converging section, the smaller end of which is joined to an elongated tubular section of uniform cross section. The improvements are applicable to both pumped and diffusion-type sample chambers.

1 Claim, 2 Drawing Sheets

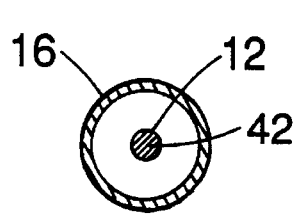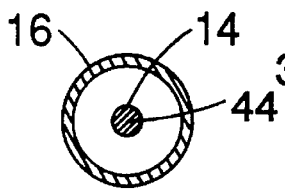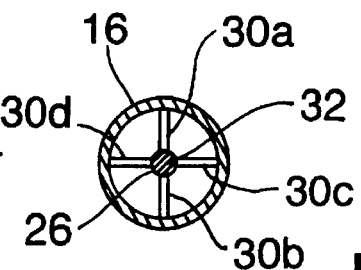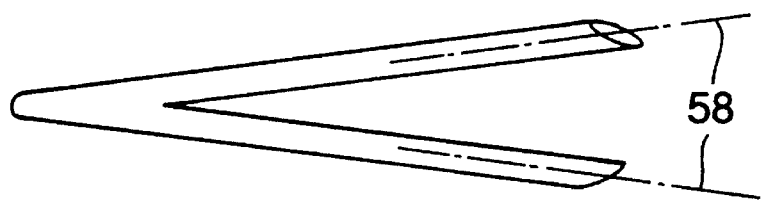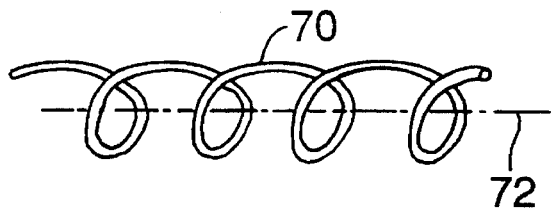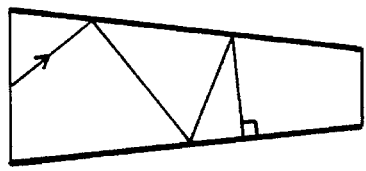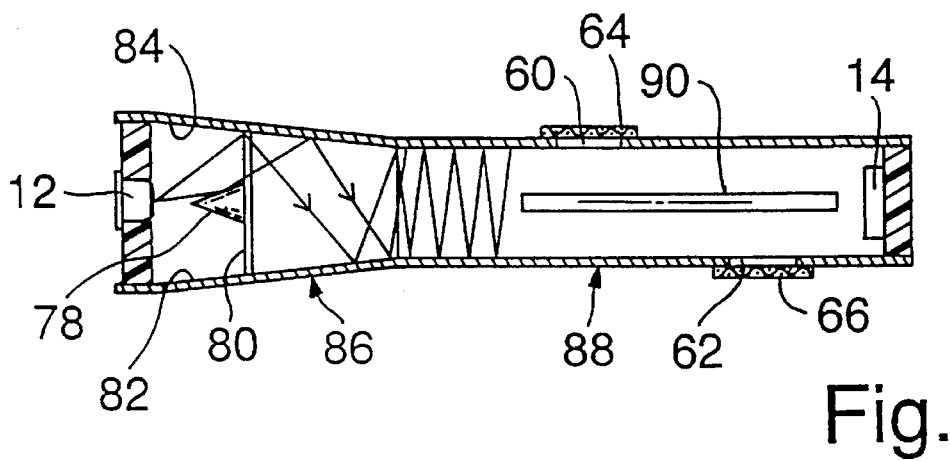

5,453,621

ENHANCED PATHLENGTH GAS SAMPLE CHAMBER

This application is a continuation of application Ser. No. 08/049,033, filed Apr. 16, 1993 now U.S. Pat. No. 5,414,264 issued May 9, 1995.

BACKGROUND OF THE INVENTION

1. Field of the Invention

The present invention is in the field of gas analysis and more specifically relates to an improvement in gas sample chambers that are used in non-dispersive infrared gas analyzers.

2. The Prior Art

In Japanese Publication (Kokai) No. 59-173734(A) Miyazaki describes a tubular gas sample chamber having the shape of a corkscrew, having a source of radiation at one end and a detector of radiation at the other end. Gas is pumped through the gas sample chamber.

A diffusion-type gas sample chamber is shown and described in U.S. Pat. No. 5,163,332 for GAS SAMPLE CHAMBER by the present inventor. In that invention, the gas to be analyzed is permitted to diffuse into and out of the sample chamber through semipermeable membranes that cover apertures in the wall of the chamber.

An improved diffusion-type gas sample chamber is described in U.S. application Ser. No. 07/915,003 filed Jul. 16, 1992 for "Improved Diffusion-Type Gas Sample Chamber", by the present inventor. The improvement is obtained by locating both the source of radiation and the detector at one end of the chamber and by providing a specularly reflective surface perpendicular to the axis of the chamber at its other end. This arrangement effectively doubles the length of the chamber.

The present invention effects a still further improvement in gas sample chambers and can be used in pumped chambers, diffusion-type chambers, and in chambers that are folded by use of a specular reflector.

SUMMARY OF THE INVENTION

The main object of the present invention is to provide an increased average pathlength for radiation as it travels from the source to the detector through the gas sample chamber.

In accordance with the present invention, this is accomplished by inserting into the gas sample chamber an obstructing element that prevents direct transfer of radiation from the source to the detector and that functions to increase greatly the number of reflections that the radiation must undergo in traveling from the source to the detector.

In a preferred embodiment, the obstructing element has the form of a specularly-reflective rod whose longer axis is coaxial with the axis of the tubular sample chamber.

The novel features which are believed to be characteristic of the invention, both as to organization and method of operation, together with further objects and advantages thereof, will be better understood from the following description considered in connection with the accompanying drawings in which several preferred embodiments of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 2 is an elevational view in the direction 2—2 indicated in FIG. 1 showing the source of radiation;

FIG. 3 is an elevational view in the direction 3—3 of FIG. 1 showing the detector of the present invention;

FIG. 4 is an elevational view in the direction 4—4 indicated in FIG. 1 showing the use of a spider to support the obstructing element of the present invention;

FIG. 6 is an enlarged perspective view showing the obstructing element used in FIG. 5;

FIG. 9 is a perspective view showing an alternative embodiment of the obstructing element of the present invention;

FIG. 10 is a diagram illustrating the use of converging walls to increase the inclination of rays reflected between the converging walls; and, FIG. 11 is a side elevational cross sectional view showing an alternative embodiment of the present invention.

DETAILED DESCRIPTION OF THE PREFERRED EMBODIMENT

It should be noted at the outset that the purpose of the present invention is to increase the average pathlength of radiation passing through the gas sample chamber from a source 12 of radiation to a detector 14. Broadly speaking, this is accomplished by inserting into the gas sample chamber an obstructing element that interrupts the more direct modes of transmission thereby forcing more of the radiation into modes of transmission that involve a greater number of reflections from the wall of the chamber and from the obstructing element. Necessarily then, the efficiency of the gas sample chamber of the present invention suffers. In most applications this is not a serious problem because, with the passage of time, the available sources are becoming more powerful, and the available detectors are becoming more sensitive. In this connection, it is also important to recall that the sensitivity of the gas analyzer depends, not on the strength of the signals, but on the effective or average pathlength through the gas sample chamber.

Figure 1:
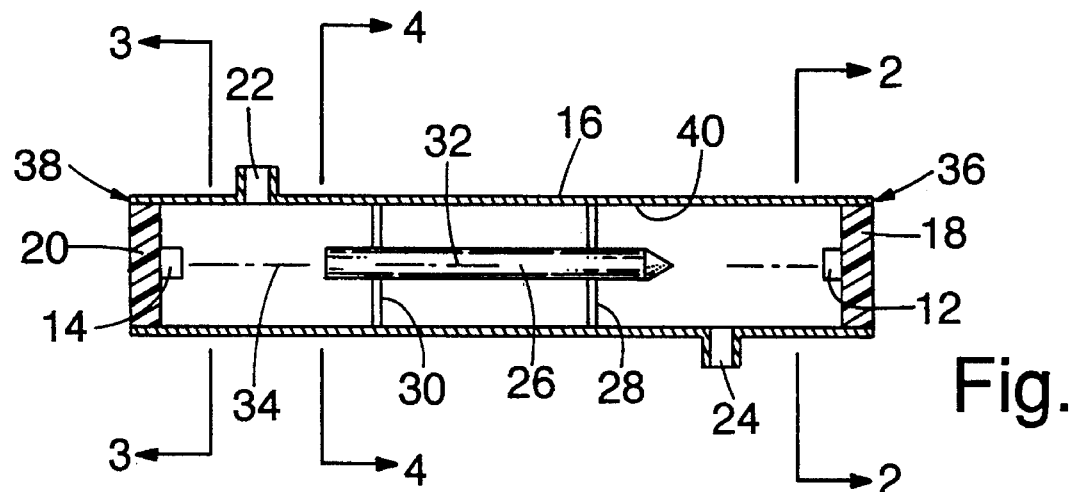
FIG. 1 is a side elevational view partly in cross section showing a first preferred embodiment of the enhanced pathlength gas sample chamber of the present invention.

FIG. 1 shows a first preferred embodiment of the present invention in which the gas sample chamber has the form of a tube 16 having a first end 36, a second end 38, and an axis 34. A source 12 of radiation is mounted on a plug 18 that is located at the first end 36 of the tube 16. A detector 14 of radiation is mounted on a plug 20 which is located at the second end 38 of the tube 16. The inner surface 40 of the tube 16 is specularly reflective. Off-axis rays of radiation from the source 12 are reflected back and forth as they progress toward the second end 38 of the tube 16, and an appreciable amount of the radiation falls on the detector 14. The gas to be analyzed is introduced through the gas inlet port 22 and flows out through the gas outlet port 24. In practice the gas is made to flow by the use of a pump which either draws or pushes the gas through the chamber. While the gas to be analyzed is present in the chamber, the radiation from the source 12 passes through it, and a portion of the radiation is absorbed by the gas. The amount of absorption that takes place is related to the concentration of the gas to be analyzed.

FIG. 2 is a front elevational view in the direction 2—2 indicated in FIG. 1. FIG. 2 shows the center 42 of the source of radiation 12. Similarly, FIG. 3 is a front elevational view in the direction 3—3 indicated in FIG. 1 and shows the center 44 of the detector 14.

As mentioned above, it is undesirable for radiation to travel along a ray extending from the center 42 of the source 12 to the center 44 of the detector 14, because that is the shortest possible pathlength. It is highly desirable, instead, that the off-axis radiation be used in preference so that a longer pathlength can be achieved. Accordingly, an obstructing element 26 is mounted with its axis 32 collinear with a ray joining the center 42 of the source with the center 44 of the detector. In the first preferred embodiment, this ray coincides with the axis 34 of the tube 16.

In the embodiment shown in FIG. 1, the obstructing element 26 is a thin rod having a specularly reflective surface. The obstructing element 26 is mounted on the spiders 28 and 30 shown in FIG. 1. FIG. 4 also shows the arrangement for mounting the obstructing element 26 in the tube 16. As seen in FIG. 4, the obstructing element 26 is supported and held in place by the spider legs 30a, 30b, 30c, and 30d.

Figure 5:
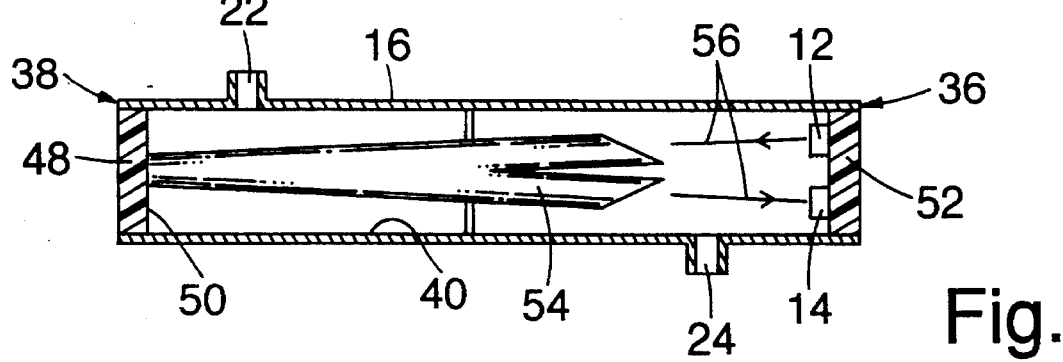
FIG. 5 is a side elevational view partly in cross section showing a second preferred embodiment of the present invention.

The second preferred embodiment shown in FIG. 5 resembles the first preferred embodiment in FIG. 1 in that the gas to be analyzed is drawn in through the gas inlet port 22 and is exhausted from the gas outlet port 24. Unlike the embodiment of FIG. 1, in the embodiment of FIG. 5, both the source 12 of radiation and the detector 14 are mounted on the plug 52 at the first end 36 of the tube 16. The opposite end 38 of the tube 16 is closed by the wall 48, and the inwardly facing surface 50 of the wall 48 is specularly reflective.

The ray 56 in FIG. 5 is the path of radiation from the center of the source 12 to the center of the detector 14 that radiation would take in the absence of the obstructing element 54. This path 56 corresponds to a direct path between the source and detector and consequently is the shortest path between those elements. Since it is desired to obscure such direct paths, the element 54 is inserted into the tube 16 so that the axis 58 of the obstructing element 54 (as best seen in FIG. 6) is collinear with the ray 56. In this manner, direct transmission from the source 12 to the detector 14 is eliminated by the obstructing element 54.

In the limit, if the source 12 and the detector 14 were brought closer together, the obstructing element 54 of FIG. 5 would assume the shape of the obstructing element 26 of FIG. 1.

Figure 7:
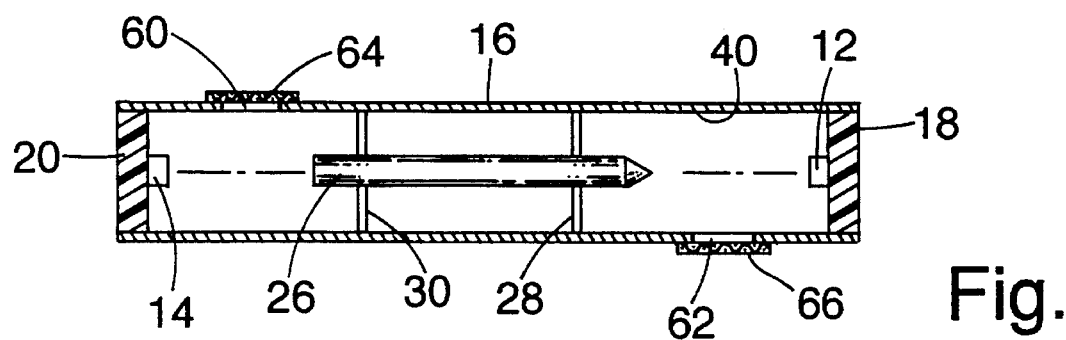
FIG. 7 is a side elevational view partially in cross section showing a third preferred embodiment of the present invention.
Figure 8:
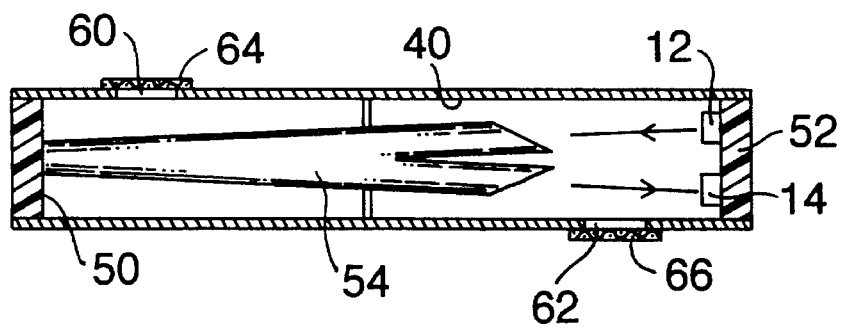
FIG. 8 is a side elevational view partly in cross section showing a fourth preferred embodiment of the present invention.

The major difference between FIGS. 1 and 5 and FIGS. 7 and 8 respectively is that in FIGS. 1 and 5 the gas to be analyzed is drawn in through the gas inlet port 22 and exhausted through the gas outlet port 24; in contrast, in the embodiments of FIGS. 7 and 8, the gas to be analyzed enters and leaves the gas sample chamber by the action of diffusion, which requires no pump. To enable the desired diffusion to occur, filtering apertures 60 and 62 are provided in the wall of tube 16, and these filtering apertures are covered by sheets 64 and 66 of a semipermeable membrane.

The sheets 64 and 66 of semipermeable membrane permit the gas in question to diffuse freely in and out of the gas sample chamber, while at the same time they prevent unwanted particles, such as dust and droplets of fluids from entering the gas sample chamber.

The fourth preferred embodiment shown in FIG. 8 is similar to the second preferred embodiment shown in FIG. 5 except for the manner in which the gas to be analyzed enters the gas sample chamber.

FIG. 9 shows yet another embodiment for the obstructing element. In this embodiment the obstructing element 70 has the form of a helix that extends along the axis 72.

The obstructing element can take a number of different forms, as seen above. The cross section of the obstructing element may be circular, square, hexagonal or almost any other desired shape. The exposed surface of the obstructing element should be highly reflective or specularly reflective so as to reduce loss of energy by absorption. Clearly, not all of the obstructing elements will result in the same optical efficiency, i.e., the same power reaching the detector. Each of the obstructing elements will result in a different efficiency and each will result in a different average pathlength. The evaluation of these different structures has not at this time been completed.

It can be shown that the pathlength traveled by a ray reflecting between parallel walls is L sec B where L is the length of the chamber and B is the inclination of the ray with respect to the wall. Note that this pathlength is independent of the separation between the parallel walls. Thus, to obtain a large pathlength, the rays should be at a steep inclination when they enter a parallel-walled chamber.

It is also well-known that when an off-axis ray enters a chamber having converging walls, the inclination of the ray will increase on each successive reflection. In fact, at some point the ray will return by successive reflections to the larger end of the converging chamber, as shown in FIG. 10.

The use of converging walls to increase the inclination of rays forms the basis of the alternative embodiment of FIG. 11. The chamber of FIG. 11 includes a converging section 86, the smaller end of which is joined to a parallel-walled section 88. Within the converging section, a specularly-reflective obstructing element 78 is mounted on a spider 80. The obstructing element 78 has a pointed shape, as best seen in FIG. 11, and is mounted so as to point toward the center of the source of radiation 12. The obstructing element 78 not only serves to block the near-axial rays from the source 12, but also serves to increase the inclination of those rays. The inclination of those rays is further increased by the converging surfaces 82 and 84. Likewise, those rays emitted by the source 12 at such a large inclination that they do not strike the obstructing element 78 also undergo an increase in inclination as they travel by successive reflections between the converging surfaces 82 and 84.

The length of the converging section of the chamber is carefully chosen so that the incoming rays are not reflected back out, but instead enter the parallel-wailed portion at very steep angles of inclination, which they maintain as they progress toward the detector 14.

Either or both of the obstructing elements 78 and 90 may be omitted from the embodiment shown in FIG. 11, although omitting either will result in a shorter average pathlength. Also, the optical system of FIG. 11 is applicable to both pumped and diffusion-type sample chambers.

Thus, there has been described a novel gas sampgle chamber in which there is included an obstructing element the purpose of which is to interfere with and break up the similar modes of transmission into the higher order modes in which a much greater number of back and forth reflections occur, thereby to increase the average pathlength on which the sensitivity of the analyzer depends.

The foregoing detailed description is illustrative of several embodiments of the invention, and it is to be understood that additional embodiments thereof will be obvious to those skilled in the art. The embodiments described herein together with those additional embodiments are considered to be within the scope of the invention.

What is claimed is:

1. An enhanced pathlength gas sample chamber for transmitting radiation through gases present in the chamber, comprising in combination:

an elongated hollow tube having an axis, having a first end and a second end, and having an inner surface that is specularly-reflective;

a hollow converging section having an axis, having a larger end and a smaller end, and having an inner surface that is specularly reflective, the smaller end of said hollow converging section affixed to the first end of said elongated hollow tube with the axis of said hollow converging section collinear with the axis of said elongated hollow tube;

said elongated hollow tube including a plurality of filtering apertures arrayed along said elongated hollow tube for improving the diffusion into and out of the space within said elongated hollow tube;

a sheet of a semipermeable membrane covering each of said plurality of filtering apertures, said semipermeable membrane permitting gases to diffuse through it under ambient pressure into and out of the space within said hollow elongated tube and preventing airborne particles larger than a predetermined size from entering said space;

a source of radiation having a center;

a detector of radiation;

means for mounting said source of radiation proximate the larger end of said hollow converging section on the axis thereof; and, means for mounting said detector of radiation proximate the second end of said elongated hollow tube on the axis thereof.

* * * * *